United States Patent [19]

Bowden

[11] Patent Number: 4,638,091

[45] Date of Patent: Jan. 20, 1987

[54] CHEMICAL PROCESS

[75] Inventor: Roy D. Bowden, Warrington, England

[73] Assignee: Imperial Chemical Industries PLC, London, England

[21] Appl. No.: 700,384

[22] Filed: Feb. 11, 1985

[30] Foreign Application Priority Data

Feb. 17, 1984 [GB] United Kingdom ................. 8404225

[51] Int. Cl.$^4$ ..................... C07C 85/08; C07C 45/00
[52] U.S. Cl. .................................. 564/473; 564/472; 568/490; 568/466; 568/465
[58] Field of Search ................ 564/472, 473; 568/490, 568/466, 465

[56] References Cited

U.S. PATENT DOCUMENTS 4,190,601 2/1980 Decker et al. ..................... 564/473

FOREIGN PATENT DOCUMENTS 2221844 10/1972 Fed. Rep. of Germany ...... 568/466

Primary Examiner—Charles F. Warren
Assistant Examiner—R. A. Picard
Attorney, Agent, or Firm—Cushman, Darby & Cushman

[57] ABSTRACT

A method for the preparation of a fluorinated amine of the formula:

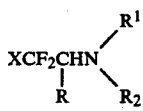

wherein X represents hydrogen or fluorine, R represents hydrogen, lower alkyl, difluoromethyl or trifluoromethyl and each of $R^1$ and $R^2$, independently, represents hydrogen or lower alkyl, which comprises reacting a carbonyl compound of the formula:

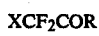

at an elevated temperature with a nitrogenous base of the formula:

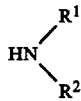

and hydrogen in the presence of a hydrogenation catalyst.

5 Claims, No Drawings

CHEMICAL PROCESS

This invention relates to a chemical process and more particularly to a method for the preparation of fluorinated amines.

Trifluoroethylamine and related compounds have been proposed for use as heat pump working fluids. The methods that have been proposed for making trifluoroethylamines have generally not been satisfactory for commercial operation because they involve the use of costly or intractable starting materials or intermediates. These methods include the amination of trifluoroethyl chloride and the hydrogenation of trifluoroacetonitrile, an extremely toxic and easily polymerised material.

It has now been found that trifluoroethylamine and other related fluorinated amines may readily be prepared by the reductive amination of the corresponding carbonyl compounds.

Accordingly, the invention provides a method for the preparation of a fluorinated amine of the formula:

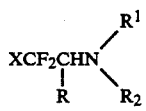

wherein X represents hydrogen or fluorine, R represents hydrogen, lower alkyl, difluoromethyl or trifluoromethyl and each of $R^1$ and $R^2$, independently, represents hydrogen or lower alkyl, which comprises reacting a carbonyl compound of the formula:

at an elevated temperature with a nitrogenous base of the formula:

and hydrogen in the presence of a hydrogenation catalyst.

The expression "lower alkyl" used herein means an alkyl radical containing from one to four carbon atoms.

As examples of carbonyl compounds which may be used in the method of the invention there may be mentioned trifluoroacetaldehyde, difluoroacetaldehyde and hexafluoroacetone.

Nitrogenous bases which may be used include ammonia, methylamine, ethylamine, dimethylamine and diethylamine.

Hydrogenation catalysts which may be used in accordance with the invention include metals of Group VIII of the Periodic Table such as rhodium, rhenium, nickel, cobalt and ruthenium. The metals may be employed in elemental form or as compounds, for example metal salts or oxides or metal complexes.

The carbonyl compound may be reacted with the base and hydrogen in the liquid phase, for example in an aqueous medium optionally containing an organic solvent.

Either a homogeneous or heterogeneous catalyst may be employed. In a homogeneous system, a catalytic metal salt or complex may be dissolved in the liquid medium whilst a heterogeneous system may use a catalytic metal in the form of a gauze or powder or a supported catalyst, suitable supports being carbon, alumina, aluminium fluoride and calcium sulphate.

Suitable reaction temperatures are generally, though not exclusively, above 100° C., for example about 150° C., whilst the pressure can be atmospheric or higher. The reaction may be operated as a continuous or batch process and the amine product may be isolated and purified using conventional techniques.

The method of the invention is particularly suitable for the preparation of 2,2,2-trifluoroethylamine and its N-lower alkyl and N,N-di (lower alkyl) derivatives by reacting trifluoroacetaldehyde with ammonia or the appropriate amine.

The trifluoroacetaldehyde used in the method of the invention may be obtained in known manner, for example by reacting trichloroacetaldehyde with a stoichiometric excess of hydrogen fluoride at an elevated temperature, for example about 350° C., in the presence of a fluorination catalyst, for example chromia. It is a particularly advantageous feature of the invention that trifluoroacetaldehyde obtained in this way may, after neutralisation of the reaction mixture with ammonia or an appropriate amine, be hydrogenated in accordance with the invention without first being purified or dried.

Thus, in a preferred embodiment of the invention, trichloroacetaldehyde, a readily available starting material, is perfluorinated by reaction with hydrogen fluoride and the reaction product, after being dissolved in a liquid, especially aqueous, medium, is contacted with ammonia or a primary or secondary lower alkyl amine, hydrogen and a hydrogenation catalyst to give the desired trifluoroethylamine compound. A convenient method of isolating the trifluoroethylamine is to subject the reaction product to steam distillation, the desired product being collected in the distillate whilst any unchanged trifluoroacetaldehyde remains in the still residues.

The invention is illustrated but not limited by the following Examples.

EXAMPLE 1

Into the bottom of a vertical 2.5 cm diameter Inconel reactor tube containing pelleted chromia were passed hydrogen fluoride (893 mls/min, measured as gas) nitrogen (40 mls/min) and vaporised chloral (0.73 mls/min, measured as liquid). The catalyst had a bed length of 43 cm and was held at 370° C. The contact time was 5 secs.

The off-gases were passed into water to form a solution.

250 mls of this solution containing 9 g fluoral were charged to a 400 ml polythene beaker equipped with stirrer and held in an ice bath. Gaseous methylamine was bubbled into the solution keeping the temperature below 30° until the pH reached approximately 6.5. This solution was charged to a 1 liter Baskerville autoclave mixed with 2 g Ni powder, purged with nitrogen and then pressurised with $H_2$. The vessel was heated at 150° C. under 12 bar pressure of hydrogen for 4 hours, then cooled. The reaction product was distilled (without filtration) using a 12" nickel-mesh packed vacuum jacketed distillation column.

The fraction bp. 50°–51° was a colourless mobile liquid, confirmed by $F^{19}$ NMR and $H^1$ NMR as N-methyl-2,2,2-trifluoroethylamine. (Yield 8.2 g=79%).

EXAMPLES 2-4

The solution prepared in Example 1 was taken to pH 6.5 by addition of aqueous ammonia solution and reacted with hydrogen under the conditions specified in the following table.

Analysis was carried out by GC using Poropak Q at 180° and by $F^{19}$ NMR spectroscopy.

Distillation of a filtered bulked sample of mixed final products (from these and several other runs under similar conditions) gave a colourless mobile liquid bp 42° compared directly with an authentic sample of trifluoroethylamine using $F^{19}$ NMR, $H^1$ NMR, MS and IR spectroscopies.

TABLE 1

| | Catalyst | Weight | Temp | Pressure | Time | % Organics as trifluoroethylamine |
|---|---|---|---|---|---|---|
| 2 | Ni | 2 g | 150 | 9 bar | 3.8 hrs | 94% |
| 3 | Ni | 2 g | 150 | 13 bar | 2.1 hrs | 60% |
| 4 | Ni | 2 g | 150 | 13 bar | 3.0 | 92% |

I claim:

1. A method for the preparation of a fluorinated amine of the formula:

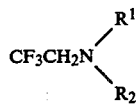

wherein each of $R^1$ and $R^2$, independently, represents hydrogen or lower alkyl, which comprises the steps of
   (a) reacting trichloroacetaldehyde with hydrogen flouride at an elevated temperature in the presence of a fluorination catalyst to form trifluoroacetadehyde,
   (b) dissolving the trifluoroacetaldehyde in an aqueous medium, and
   (c) contacting the aqueous solution of trifluoroacetaldehyde with a nitrogenous base of the formula:

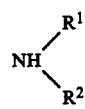

and hydrogen in the presence of a hydrogenation catalyst.

2. A method according to claim 1 wherein the nitrogenous base is ammonia.

3. A method according to claim 1 wherein the hydrogenation catalyst comprises a Group VIII metal.

4. A method according to claim 1 wherein trifluoroacetaldehyde is reacted with ammonia and hydrogen in the presence of a hydrogenation catalyst.

5. A method according to claim 4 wherein the hydrogenation catalyst contains nickel.

* * * * *